(12) United States Patent
Fiori et al.

(10) Patent No.: US 9,527,918 B2
(45) Date of Patent: Dec. 27, 2016

(54) ANTIBACTERIAL POLYMERS AND METHOD FOR OBTAINING THE SAME

(71) Applicant: PARX PLASTICS BV, Lb Nieuwerkerk ad Ijssel (NL)

(72) Inventors: Michele Fiori, Bologna (IT); Nunzia Nocerino, Ercolano (IT); Rosanna Capparelli, Portici (IT); Andrea Fulgione, Portici (IT); Michael Van Der Jagt, Rotterdam (NL); Chiara Medaglia, Portici (IT); Marco Marchetti, Montefiore Dell'Aso (IT); Norberto Roveri, Bologna (IT); Rocco Mercuri, Bevagna (IT); Marco Lelli, Monghidoro (IT); Francesca Rinaldi, Ferrara (IT)

(73) Assignee: PARX PLASTICS BV, Nieuwerkerk ad Ijssel (NL)

( * ) Notice: Subject to any disclaimer, the term of this patent is extended or adjusted under 35 U.S.C. 154(b) by 0 days.

(21) Appl. No.: 13/984,782

(22) PCT Filed: Mar. 28, 2013

(86) PCT No.: PCT/IB2013/052491
§ 371 (c)(1),
(2) Date: Oct. 31, 2013

(87) PCT Pub. No.: WO2014/155156
PCT Pub. Date: Oct. 2, 2014

(65) Prior Publication Data
US 2014/0296442 A1    Oct. 2, 2014

(51) Int. Cl.
| | |
|---|---|
| *C08F 10/06* | (2006.01) |
| *C08F 12/08* | (2006.01) |
| *C08F 14/06* | (2006.01) |
| *C08G 61/10* | (2006.01) |
| *C08G 63/68* | (2006.01) |
| *C08G 64/24* | (2006.01) |
| *C08G 69/26* | (2006.01) |
| *C07K 16/28* | (2006.01) |
| *A61K 39/395* | (2006.01) |
| *C07H 21/04* | (2006.01) |
| *C12N 15/117* | (2010.01) |
| *A61K 39/00* | (2006.01) |
| *C07K 14/705* | (2006.01) |
| *C07K 16/18* | (2006.01) |
| *C12N 5/10* | (2006.01) |
| *C12N 5/12* | (2006.01) |
| *C12N 15/63* | (2006.01) |

(52) U.S. Cl.
CPC ....... *C07K 16/2896* (2013.01); *A61K 39/3955* (2013.01); *A61K 39/39533* (2013.01); *C07H 21/04* (2013.01); *C07K 16/28* (2013.01); *C12N 15/117* (2013.01); *A61K 2039/505* (2013.01); *C07K 14/705* (2013.01); *C07K 16/18* (2013.01); *C07K 2316/96* (2013.01); *C07K 2317/21* (2013.01); *C07K 2317/24* (2013.01); *C07K 2317/33* (2013.01); *C07K 2317/34* (2013.01); *C07K 2317/51* (2013.01); *C07K 2317/515* (2013.01); *C07K 2317/52* (2013.01); *C07K 2317/56* (2013.01); *C07K 2317/565* (2013.01); *C07K 2317/76* (2013.01); *C07K 2317/92* (2013.01); *C07K 2317/94* (2013.01); *C12N 5/10* (2013.01); *C12N 5/12* (2013.01); *C12N 15/63* (2013.01); *C12N 2310/17* (2013.01)

(58) Field of Classification Search
CPC .......... A01N 59/16; C08F 10/06; C08F 12/08; C08F 14/06; C08F 2/44; C08G 63/681; C08G 64/24; C08G 69/26; C08K 5/0058; C08K 2003/0893
See application file for complete search history.

(56) References Cited

U.S. PATENT DOCUMENTS

| | | | |
|---|---|---|---|
| 3,862,066 A * | 1/1975 | Reiter et al. ............... 524/728 |
| 6,605,751 B1 | 8/2003 | Gibbins et al. | |
| 7,625,957 B2 | 12/2009 | Harren et al. | |
| 2004/0010215 A1 | 1/2004 | Gibbins et al. | |
| 2005/0171235 A1 | 8/2005 | Harren et al. | |
| 2005/0226931 A1 | 10/2005 | Gibbins et al. | |

(Continued)

FOREIGN PATENT DOCUMENTS

| | | |
|---|---|---|
| CN | 101372527 A | 2/2009 |
| CN | 101658485 A | 3/2010 |

(Continued)

OTHER PUBLICATIONS

Rodríguez-Tobías et al, Journal of Applied Polymer Science vol. 127 pp. 4708-4718 published online Jun. 2012.*

(Continued)

*Primary Examiner* — Irina S Zemel
*Assistant Examiner* — Jeffrey Lenihan
(74) *Attorney, Agent, or Firm* — Pearne & Gordon LLP

(57) ABSTRACT

The invention relates to polymers selected from among polypropylene (PP), polycarbonate (PC), acrylonitrile-butadiene-styrene (ABS), polyvinylchloride (PVC) and polyethylene terephthalate (PET), nylon and polystyrene, having antibacterial properties, wherein the antibacterial effect is obtained by adding a zinc salt selected from among: zinc PCA, zinc oxide, zinc hydroxide, zinc pyrrolidone or zinc pyrithione during the process of polymerization of the monomers. The antibacterial polymers are used to prepare products intended to enter into contact with the skin.

5 Claims, No Drawings

(56) References Cited

U.S. PATENT DOCUMENTS

2007/0149694 A1   6/2007  Krishnan
2009/0269379 A1*  10/2009 Herbst ............... A01N 25/34
                                                       424/404
2010/0034882 A1   2/2010  Gibbins et al.

FOREIGN PATENT DOCUMENTS

| CN | 102031584 A   | 4/2011  |
| CN | 102675817 A   | 9/2012  |
| CN | 102787497 A   | 11/2012 |
| JP | 2822509 B2 *  | 11/1998 |
| JP | 2007016334 A  | 1/2007  |
| JP | 2007169799 A  | 7/2007  |
| WO | 03090799 A1   | 11/2003 |
| WO | WO-2008/024509 A2 * | 2/2008 |

OTHER PUBLICATIONS

Ministero Dello Sviluppo Economico; Rapporto di Ricerca, dated Jun. 28, 2013(Search Report and Written Opinion prepared by European Patent Office with reference to the corresponding Italian patent application No. MI2013A000469 filed on Mar. 28, 2013); pp. 1-7.

Lu Xiuping et al., "Preparation of Antibacterial Composite Latex of Nanometer ZnO and Antibacterial Effect Thereof", Journal of Tianjin University of Science & Technology, vol. 21, No. 4, Dec. 31, 2006, pp. 1-4 and 8 (English Abstract enclosed).

* cited by examiner

ANTIBACTERIAL POLYMERS AND METHOD FOR OBTAINING THE SAME

FIELD OF THE INVENTION

The present invention relates to polymers having antibacterial properties and the uses thereof for preparing products intended to come into contact with the skin. The invention also relates to a process for preparing such polymers.

BACKGROUND OF THE INVENTION

Bacteria are to be found everywhere dispersed in the environment and can be beneficial or else carry diseases. The latter are normally transmitted by diseased people or animals, contaminated water and food and other external sources of contamination.

It is possible to be contaminated with bacteria responsible for the development of pathologies through contact with objects or surfaces previously manipulated by people or animals that are carriers of such bacteria.

The problem of safety against bacterial proliferation has by now reached a global dimension. The development of different types of pathogenic bacteria on the surfaces of objects/products is favoured by particular environmental conditions.

Generally, microorganisms must reach certain concentrations in order to cause damage to the body, i.e. to provoke diseases. It thus appears important to prevent conditions from arising which are suitable for their development. Besides the normal rules of hygiene, by now well-established, there is an increasingly widespread need to develop materials with intrinsic antibacterial properties to be used to prepare widely used consumer products, intended in particular to enter into contact with the skin. Combining common rules of hygiene and the use of antibacterial materials enables optimal results to be achieved in terms of reducing bacterial contamination and thus the pathologies connected thereto.

Nowadays, thermoplastic polymers are the materials most widely used to manufacture products in any sector. It thus becomes important to have at our disposal products made of plastic material capable of hindering bacterial proliferation.

Historically speaking, the antibacterial properties of silver have been known since antiquity.

In fact, even though bacteria were obviously unknown, the antibacterial and curative effects of some metals such as silver were known as far back as antiquity.

Starting from these first applications we eventually arrived at the technique of combining nano-particles of silver, or of colloidal silver (liquid suspension of microscopic particles of silver) with polymeric plastic materials, in order to impart antiseptic and antibacterial properties to the latter.

However, it is well known that the prolonged use of colloidal silver or silver particles can provoke a chronic intoxication called "argyria".

Moreover, there is ample scientific documentation regarding the side effects of colloidal silver, which can cause skin necrosis if maintained in contact with the skin for a long time.

However, there are various metals which have antimicrobial properties, for example copper, nickel and zinc. Copper and nickel, however, are subject to strong legislative restrictions because of their high toxicity.

The toxicity of the free metallic zinc is well known, as are the neurological problems it can induce. Nonetheless, zinc ion-based compounds are less toxic than metallic zinc and retain antibacterial properties.

Over the last few years numerous studies have confirmed the antimicrobial and antiviral properties of zinc ions, especially against Gram+ bacteria such as *Staphylococcus Aureus*, one of the most common pathogenic bacteria responsible for skin infections, and against the principal bacteria of the oral cavity, such as Streptococci and Actinomycetes.

Zinc ions in fact possess bacteriostatic properties, i.e. they inhibit the bacterial growth because they are able to penetrate into bacterial cells, blocking different biological processes that are fundamental for the survival of the bacteria themselves.

Polymers having antibacterial properties are known; they are obtained by mixing the polymer with zinc salts and the antiseptic properties thereof are due to the ions of these metals. Although it achieves the intended result, namely, that of imparting to the polymers antiseptic and antibacterial properties belonging to the metal ion, thus combating the proliferation of microbes and bacteria, mixing the polymeric macromolecule with zinc salts poses a major disadvantage.

This disadvantage is tied to the release of zinc ions over time, due to the fact that the salts of these metals are simply mixed with the polymer and not incorporated into the polymeric structure. In fact, even if the mixing is done in an optimal manner, over time there occur phenomena whereby the metal ions are released in quantities exceeding the limits allowed by applicable European legislation, which regulates the maximum limits of metals that can migrate from a polymer to the surrounding environment. With regard to the zinc ion, this legislation sets the maximum migration limit at a value of 21 ppm.

In light of the considerations set forth above, in the art there exists a need to provide polymers with antibacterial and antiseptic properties to be used to manufacture products intended to come into contact with human or animal skin, characterized by low toxicity and by a release of zinc ions that is lower than the legal limits.

SUMMARY OF THE INVENTION

In general terms, the present invention relates to a polymer having antibacterial and antiseptic properties obtained or obtainable by adding at least one zinc salt to a solution or dispersion, in an aqueous or organic solvent, of the monomers used to synthesize the polymer. Alternatively, the at least one zinc salt can be added during the reaction of polymerization of the starting monomers.

The invention also relates, in general terms, to a process for obtaining the antibacterial polymer comprising a step of adding at least one zinc salt to the solution or dispersion, in an aqueous or organic solvent, of the monomers used to synthesize the polymer by means of a polymerization reaction. In particular, this addition takes place before the start of the polymerization reaction or else during the reaction and before the completion thereof. The invention also relates to an antibacterial and antiseptic product obtained from the antibacterial polymer of the invention, for example by means of extrusion, moulding (for example, male-female moulding, injection moulding), hot forming, etc. This product can be, for example, a mouse for a PC, a computer keyboard, a cover for phones and tablets, a door handle, a plastic handrail, an antibacterial covering for panic exit devices, antibacterial film for surfaces that must have a high degree of cleanliness, eyeglass frames, etc.

DETAILED DESCRIPTION OF THE INVENTION

The present invention relates to a process for preparing an antibacterial and antiseptic polymer, comprising the steps of:
a) solubilising or dispersing at least one zinc salt in an organic or aqueous solvent;
b) adding the dispersion or solution thus obtained to the solution or dispersion of at least one monomer in an organic or aqueous solvent;
c) polymerizing the at least one monomer.

All of the percentages indicated in the patent application are to be understood as percentages by weight calculated relative to the final weight of the antibacterial polymer it is desired to obtain.

The antibacterial polymer is a thermoplastic polymer, for example polypropylene (PP), polycarbonate (PC), acrylonitrile-butadiene-styrene (ABS), polyvinylchloride (PVC), polyethylene terephthalate (PET), nylon and polystyrene.

If it is desired to make an antibacterial polypropylene, the at least one monomer is propylene, which is subjected to polymerization according to step c) of the process following the addition of the at least one zinc salt. The polymerization of the propylene is conducted with the normal techniques known in the art which use appropriate catalysts to obtain isotactic or syndiotactic propylene. The polycarbonate is obtained from the polymerization of at least one monomer diol selected for example from among: bisphenol A, 1,1-bis 1,1-bis(4-hydroxyphenol)cyclohexane, dihydroxybenzophenone and tetramethyl cyclobutanediol with a source of carbonate groups, for example phosgene and diphenyl carbonate. The conditions of polymerization are known in the art and will thus not be further illustrated. ABS is a copolymer, i.e. a polymer made by polymerizing not a single monomer, but rather a number of monomers.

To make an antibacterial ABS polymer, acrylonitrile, butadiene and polymerized styrene (polystyrene) are mixed in a given range of percentages:
acrylonitrile, in a percentage comprised between 12% and 40%, preferably between 20% and 35%.
butadiene, in a percentage comprised between 2% and 35%, preferably between 10% and 20%.
polymerized styrene (polystyrene) in a percentage comprised between 30% and 70%, preferably between 40% and 60%.

To make an ABS polymer with antibacterial properties, suitable aliquots of the different components are taken in the proportions indicated and polymerized using the traditional methods for the polymerization and synthesis of ABS polymers.

The polystyrene used to prepare the ABS can already possess antibacterial properties if made and polymerized according to the process described in the present patent.

In particular, the polystyrene is obtained from the polymerization (carried out according to the processes and under the conditions known in the art) of styrene monomers, to which the dispersion or solution of the at least one zinc salt has been added.

The polyvinylchloride is obtained from the polymerization of the vinyl chloride monomer under the conditions known in the art.

The polyethylene terephthalate is obtained from the polymerization of the monomers terephthalic acid and ethylene glycol, or else dimethyl terephthalate and ethylene glycol, under the conditions known in the art.

The nylon is obtained via a condensation reaction of diamine with carboxylic acids using procedures and reaction conditions known in the art.

The at least one zinc salt is added to the dispersion or solution of the at least one monomer necessary for the polymerization, or else to the dispersion or suspension of a mixture of two or more monomers.

The solvent used to prepare the solution or dispersion of the at least one zinc salt is preferably selected from among: water, ethyl alcohol, methanol, acetone, isopropyl alcohol or a mixture of two or more solvents.

If a mixture of solvents is used, the individual solvents are preferably used in the following percentages:
water: it is used within the mixture in a percentage comprised between 5% and 100%, preferably between 20% and 100% by weight.
ethyl alcohol: it is used within the mixture in a percentage comprised between 5% and 15%, preferably between 5% and 10% by weight.
methanol: it is used within the mixture in a percentage comprised between 5% and 10%, preferably between 5% and 7% by weight.
acetone: it is used within the mixture in a percentage comprised between 3% and 70%, preferably between 10% and 65% by weight.
isopropyl alcohol: it is used within the mixture in a percentage comprised between 2% and 20%, preferably between 5% and 15% by weight.

In a preferred embodiment, the solution or dispersion of the at least one zinc salt is added one drop at a time to the solution or dispersion of the monomer. During the polymerization step c), the polymer will incorporate the at least one salt within the polymeric structure, thus imparting considerable antibacterial and antiseptic properties to the polymeric product obtained.

This is due to the use of the zinc ion-based additive, which thanks to its properties hinders and combats microbial and bacterial proliferation on the polymeric surface obtained, irrespective of the polymer used or the shape of the product obtained.

Preferably, the at least one zinc salt is selected from among: zinc PCA (zinc salt of pyrrolidone carboxylic acid), zinc oxide, zinc hydroxide, zinc pyrrolidone, zinc pyrithione or mixtures thereof.

The quantities of the at least one zinc salt added to the at least one monomer are comprised between 0.1 and 10% by weight, preferably between 0.1% and 5%, more preferably between 0.2% and 4%.

For example, the zinc PCA is used in a percentage comprised between 0.1% and 10%, preferably between 2% and 5%.

The zinc oxide is used in a percentage comprised between 0.1% and the 2%, preferably between 0.2% and the 0.6%.

The zinc hydroxide is used in a percentage comprised between 0.1% and 4%, preferably between 0.2% and 1%.

The zinc pyrithione is used in a percentage comprised between 0.1% and 2%, preferably between 0.1% and 0.7%.

The zinc pyrrolidone is used in a percentage comprised between 0.01% and 3%, preferably between 0.1% and 1%.

In a preferred embodiment, the at least one zinc salt is ZnPCA or Zn pyrithione or else a mixture thereof. In another embodiment, all the zinc salts listed above are used in a mixture.

To synthesize the polymer antibacterial of the invention, the above-specified quantities of salts are dissolved in one or more solvents as previously described.

The less soluble salts, zinc oxide and zinc hydroxide for example, are dispersed finely in a number of solvents as described above.

Once the solution or dispersion of one or more salts is obtained, this is added to the suspension or solution of the at least one monomer, or, alternatively, it is added during the polymerization process.

The at least one monomer is preferably dissolved or suspended in solvents selected from among: acetone, dichloromethane, chloroform or mixtures thereof.

Once added, the solution or dispersion of the at least one zinc salt is subjected to stirring together with the monomers of the polymer until the polymer is obtained through polymerization of the monomers. The reaction time is preferably comprised between 20 minutes and 3 hours, more preferably between 60 minutes and 90 minutes.

In a second aspect, the invention relates to an antibacterial polymer obtainable through the above-described process, wherein at least one zinc salt is dispersed within the polymeric structure, imparting antiseptic properties to the polymer.

The antibacterial polymer of the invention is characterized in that is has a release of zinc ions that is below the legal limits of 21 ppm, as shown by the release tests performed and reported hereunder. This represents a considerable advantage for the health and safety of the end user of such polymers. Moreover, the antibacterial properties of the polymer are optimal, as demonstrated by the tests conducted to measure bacterial proliferation and reported hereunder.

The antibacterial polymer of the invention is effective for controlling or eliminating the bacterial proliferation of Gram− and Gram+ bacteria, e.g. *Escherichia Coli Staphylococcus Aureus, Pseudomonas aeruginosa, Acinetobacter baum, Ent. Cloacae, C. albicans* and *Clostriudim difficile*.

The antibacterial polymers thus obtained can be used directly to prepare products with antiseptic properties or else be mixed with polymers of the same chemical nature or of a different chemical nature in order to yield an antibacterial polymer that can then be used to prepare antibacterial products.

The products can preferably be obtained by moulding (for example using a male-female mould or an injection mould), hot forming or extruding the antibacterial polymer.

Such products can be, for example, computer mice, computer keyboards, covers for phones and tablets, door handles, plastic handrails, antibacterial coverings for panic exit devices, antibacterial film for surfaces that must have a high degree of cleanliness, eyeglass frames, etc.

In a further aspect, the invention relates to a product obtainable from the antibacterial polymer by, for example, moulding (for example injection moulding and male-female moulding), hot forming or extrusion.

In a preferred embodiment, the product is prepared by bringing the antibacterial polymer to the melting point. This temperature will obviously be different depending on the polymer it is intended to use. Once molten, the latter is injected, preferably by means of specific nozzles, into a mould that has the shape of the final product it is desired to make. Once filled, the mould is then brought to a temperature comprised between 150° C. and 350° C., preferably between 160° C. and 220° C., at which point the mould is opened in order to remove the product obtained.

EXAMPLES

To make PP with antibacterial properties, one starts from the monomer propylene.

An initial quantity of propylene (50 grams) is dispersed in a mixture of solvents comprising: 10% ethyl alcohol and 90% water and having a total weight equal to 1 kg.

A solution of zinc salts comprising 2 g of ZnPCA is added to the monomer solution. The solution thus obtained is subjected to a synthesis temperature comprised between 55° C. and 65° C.

To this mixture it is necessary to add an appropriate catalyst, indispensable for polymer synthesis.

To make PVC with antibacterial properties, one starts from vinyl chloride. An initial quantity of vinyl chloride (50 grams) is dispersed in a mixture of organic solvents composed of: 9% ethyl alcohol, 10% water, 7% methanol, 60% acetone and 14% isopropyl alcohol and having a total weight equal to 1 kg.

A solution of zinc salts containing: 1 g of ZnPCA, 0.1 g of zinc oxide, 0.2 g of zinc hydroxide, 0.2 g of zinc pyrrolidone and 0.2 g of zinc pyrithione is added to the monomer solution. The mixture is heated to the synthesis temperature, comprised between 50° C. and 65° C.

To make PET with antibacterial properties, one starts from the monomer ethylene.

An initial quantity of ethylene (50 grams) is dispersed in the mixture of solvents: 10% ethyl alcohol, 80% water and 10% isopropyl alcohol, having a total weight equal to 1 kg. A solution containing: 1 g of ZnPCA, 0.2 g of zinc oxide, 0.2 g of zinc hydroxide, 0.2 g of zinc pyrrolidone and 0.2 g of zinc pyrithione is added to the monomer solution. The mixture thus obtained is heated to the synthesis temperature, comprised between 60° C. and 65° C.

To this mixture it is necessary to add an appropriate catalyst, indispensable for polymer synthesis.

To make PP with antibacterial properties, one starts from the monomer propylene.

An initial quantity of propylene (50 grams) is dispersed in a mixture of solvents comprising: 10% ethyl alcohol and 900 water and having a total weight equal to 1 kg.

A solution of zinc salts comprising: 1 g of ZnPCA, 0.2 g of zinc oxide, 0.2 g of zinc hydroxide, 0.2 g of zinc pyrrolidone and 0.2 g of zinc pyrithione is added to the monomer solution. The mixture thus obtained is subjected to a synthesis temperature comprised between 55° C. and 65° C.

To this mixture it is necessary to add an appropriate catalyst, indispensable for polymer synthesis.

To synthesize PC with antibacterial properties, one starts from two different raw materials: bisphenol A and phosgene. A quantity of 221 g of bisphenol A is dissolved in water. On completion of the dissolution process, soda is added to the solution in order to basify the solution and make the polymerization process possible.

In parallel an aqueous solution containing zinc and consisting of 2 g of ZnPCA and 0.2 g of zinc pyrithione is prepared.

The two aqueous solutions are then mixed.

A solution of phosgene (99 g) in $CH_2Cl_2$ is then prepared. The two solutions are kept separate and the synthesis of the polymer PC occurs at the interface.

The temperature at which the process takes place is comprised between 20° C. and 60° C.; in particular, a temperature comprised between 30° C. and 40° C. was used.

To make nylon with antibacterial properties, one polymerizes 116 g of hexadiethylamine with 185 g of acyl chloride of adipic acid.

The hexadiethylamine is dissolved in a suitable amount of water.

In parallel, an aqueous solution containing zinc and consisting of 2 g of ZnPCA and 0.2 g of zinc pyrithione is prepared.

The two aqueous solutions are then mixed.

The acyl chloride of adipic acid is dissolved in a suitable aliquot of organic solvent, for example chloroform.

The two solutions are kept separate and the synthesis of the nylon occurs at the interface.

The temperature at which the process takes place is comprised between 5° C. and 70° C., in this case a temperature comprised between 25° C. and 35° C. was used; at this temperature the polymerization process takes place at the interface between the two solutions.

To make polystyrene with antibacterial properties, one polymerizes the monomer styrene.

An appropriate amount of styrene (30 g) is solubilised in a suitable amount of water (1 kg).

In parallel, an aqueous solution containing zinc and consisting of 2 g of ZnPCA and 0.2 g of zinc pyrithione is prepared.

The two solutions are then joined together in the presence of suitable catalysts such as peroxides, at a polymerization temperature comprised between 50° C. and 150° C., preferably between 70° C. and 120° C.

Production of Polypropylene (PP) Covers for Phones

An initial quantity of polypropylene (PP) obtained using the previously described process is loaded at the inlet of a machine suitable for forming phone covers.

A heating apparatus brings the granules of the polymer PP to a temperature of 180° C., causing them to melt.

The mass of polymer thus prepared is then introduced into specific moulds using preheated nozzles.

The moulds (male and female) impart to the molten polymer the desired shape, which corresponds to that of phone covers.

Once moulding has taken place, the mould undergoes a cooling process which lasts a few seconds, at the end of which it is opened to enable removal of the product made. In a second preferred embodiment, a heating apparatus brings the granules of the polymer PP to a temperature of 180° C., causing them to melt.

The mass of polymer thus prepared is then injected into specific moulds using preheated nozzles.

The mould imparts the desired shape to the molten polymer. Once moulding has taken place, the mould undergoes a cooling process which lasts a few seconds, at the end of which it is opened to enable removal of the product made.

Zinc Ion Release Test

To carry out this release test, a product (for example the phone cover of the previous example) made with an antibacterial polymer described in the present patent was introduced into a beaker and completely immersed in a known volume of a food simulant.

Subsequently, the beakers thus composed were introduced into a temperature-controlled oven at 70° C. for a total time of 2 hours.

At the end of that time (defined by current legislation on specific and global migration of metals and colouring agents in products intended for contact with food), the beaker was removed from the oven. The stimulant taken from the beaker was analyzed by ICP to determine the zinc that might be present within the simulant.

The simulants used were water and 3% acetic acid.

The following table shows the migration results obtained:

| zinc migration (ppm) into the simulants used | | |
|---|---|---|
| water | acetic acid | Type of antibacterial polymer |
| <0.001 | <0.001 | PVC |
| <0.001 | <0.001 | Polystyrene |
| <0.001 | <0.001 | nylon |
| 0.100 | <0.001 | PET |
| 0.109 | 0.177 | PP |
| 0.332 | 0.332 | ABS |
| <0.001 | 0.402 | PC |

From the results obtained it can be observed that the release of zinc is less than the 21 ppm allowed by law.

Antibacterial Activity

A phone cover obtained by moulding the antibacterial polymer ABS prepared as described above was tested to evaluate the effectiveness of the polymer against the main microbial strains defined by current legislation regarding plastic products intended to come into contact with the skin.

The product was tested for 2 types of bacterial strains (*Escherichia Coli* ATCC 8739 (Gram−) and *Staphylococcus Aureus* ATCC 6538 (Gram+)) using the standard international method for evaluating the antibacterial activity of non-porous plastic surfaces.

| MICROBIAL STRAINS | Initial inoculum (cfu/ml) | Incubation at 37° C. for 24 h | Control inoculum (cfu/ml) | Moulded polymer item (cfu/ml) | Reduction log | Reduction % |
|---|---|---|---|---|---|---|
| *Escherichia coli* | $2.5 \times 10^6$ | | $6.2 \times 10^7$ | $1.0 \times 10^7$ | 0.79 | 83.87% |
| *Staphylococcus Aureus* | $1.7 \times 10^6$ | | $2.3 \times 10^7$ | $1.4 \times 10^6$ | 1.2 | 93.91% |

The initial bacterial suspensions were diluted so as to obtain a known bacterial concentration expressed in colony forming units—cfu/ml. The covers analyzed were duly sectioned in order to produce pieces of optimal dimensions for conducting the tests. These were treated with the reference microbial strains, covered with sterile polyethylene film and placed in an incubator at a temperature of 37±1° C. for 24 hours. At the end of the incubation period the samples were washed with neutralizing solution, on which the residual microbial count was determined.

The results obtained show that after 24 hours of incubation at 37° C. the polymer treated with zinc reduces the bacterial count by 83.870 (in the case of *Escherichia coli*) and 93.91% (in the case of *Staphylococcus aureus*).

These tests were repeated on the other polymers as well and the results were in line with those indicated in the table above.

The invention claimed is:

1. An antibacterial thermoplastic polymer, said antibacterial thermoplastic polymer being polyethylene terephthalate (PET) obtainable from a process comprising the steps of:
   a) solubilizing zinc PCA in at least an organic and/or aqueous solvent;
   b) adding the solution thus obtained to a solution or dispersion of at least one monomer in an organic and/or aqueous solvent;
   c) polymerizing the at least one monomer,
wherein the zinc PCA is dispersed within the polymeric structure, imparting antiseptic properties to the polymer, wherein said zinc PCA is 2-5 weight percent of said polymer.

2. A method of preparing an antibacterial product comprising the step of moulding, hot forming or extruding the polymer according to claim 1.

3. An antibacterial product obtainable from a process comprising a step of moulding, hot forming or extruding the polymer according to claim 1.

4. The product according to claim 3, selected from the group consisting of computer mice, computer keyboards, covers for phones and tablets, door handles, plastic handrails, antibacterial coverings for panic exit devices, antibacterial film for surfaces and eyeglass frames.

5. A method of preparing an antibacterial product comprising the steps of:
   (a) mixing the polymer according to claim 1 with polymers of the same or different chemical nature and
   (b) moulding, hot forming or extruding the mixture originating from step (a).

* * * * *